(12) United States Patent
Tyagi et al.

(10) Patent No.: US 7,335,767 B2
(45) Date of Patent: Feb. 26, 2008

(54) METHOD FOR PREPARATION OF CEFTIOFUR AND SALTS THEREOF

(75) Inventors: Om Dutt Tyagi, Pune (IN); Santosh Kumar Richhariya, Pune (IN); Rajesh Kumar Ramchandra Pawar, Pune (IN)

(73) Assignee: Lupin Limited, Maharashtra (IN)

( * ) Notice: Subject to any disclaimer, the term of this patent is extended or adjusted under 35 U.S.C. 154(b) by 232 days.

(21) Appl. No.: 10/694,619

(22) Filed: Oct. 27, 2003

(65) Prior Publication Data

US 2004/0132996 A1 Jul. 8, 2004

(30) Foreign Application Priority Data

Oct. 29, 2002 (IN) ....................................... 938/02

(51) Int. Cl.
*C07D 501/36* (2006.01)
(52) U.S. Cl. ..................................................... 540/227
(58) Field of Classification Search ..................... None
See application file for complete search history.

(56) References Cited

U.S. PATENT DOCUMENTS

| 4,312,986 | A | | 1/1982 | Saikawa et al. | |
|---|---|---|---|---|---|
| 4,464,367 | A | * | 8/1984 | Labeeuw et al. | 540/227 |
| 4,476,220 | A | | 10/1984 | Penfound | |
| 4,937,330 | A | | 6/1990 | Sacks et al. | |
| 5,132,419 | A | | 7/1992 | Lanz et al. | |
| 6,458,949 | B1 | | 10/2002 | Handa et al. | |
| 6,476,220 | B2 | * | 11/2002 | Kumar et al. | 540/226 |
| 2006/0058281 | A1 | * | 3/2006 | Senthilkumar et al. | 514/203 |
| 2006/0149054 | A1 | * | 7/2006 | Tyagi et al. | 540/222 |

OTHER PUBLICATIONS

ICH Harmonised Tripartite Guideline Stability Testing of New Drug Substances and Products Q1A(R2) Step 4 (Feb. 6, 2003).*

* cited by examiner

*Primary Examiner*—Mark L. Berch
(74) *Attorney, Agent, or Firm*—Ladas & Parry LLP

(57) ABSTRACT

A process for preparation of ceftiofur sodium of formula (Ib)

(Ib)

possessing high stability and having purity of more than 97% and substantially free of impurities, is disclosed. The process comprises:
i) reacting cefotaxime or its salts or its esters of formula (VI)

(VI)

wherein $R_3$ is hydrogen, an alkali or alkaline earth metal, or an easily hydrolysable ester, with thiofuroic acid, employed in a molar proportion of 1.5 to 3.0 moles per mole of compound (VI), in the presence of acetonitrile as solvent and in the presence of large excess of methanesulfonic acid, employed in molar proportions of 12 to 18 moles per mole of compound (VI), and at a temperature of between $-5°$ C. to $30°$ C. to give after necessary neutralization of the alkali or alkaline earth metal or removal of the ester group of the 4-carboxylic acid function, wherever applicable, ceftiofur of formula (Ia), possessing high stability and having purity of more than 97% and substantially free of impurities;

(Ia)

ii) converting the ceftiofur of formula (Ia) thus obtained to its salt with an organic amine by treating a solution of ceftiofur in a mixture of water and a water-miscible organic solvent with an organic amine, at a temperature ranging from $-10°$ C. to $10°$ C.;
iii) reacting of the amine salt thus obtained with a sodium metal carrier in a mixture of water and water-miscible organic solvent and in presence of sodium hydrogen sulfite to give ceftiofur sodium of formula (Ib).

9 Claims, No Drawings

METHOD FOR PREPARATION OF CEFTIOFUR AND SALTS THEREOF

FIELD OF THE INVENTION

The present invention relates to an improved method for preparation of ceftiofur and its salts of formula (I),

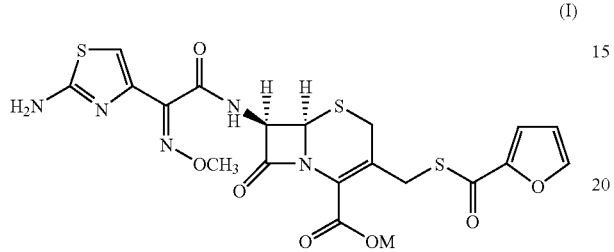

(I)

wherein M is either hydrogen, sodium or represents an easily hydrolysable ester group, of high stability, high purity and substantially free of impurities

BACKGROUND OF THE INVENTION

7-[2-(2-amino-4-thiazolyl) glyoxylamido] 3-(mercaptomethyl)-8-oxo-5-thia-1-azabicyclo-[4.2.0]oct-2-ene-2-carboxylic acid, of formula (Ia), generically known as ceftiofur

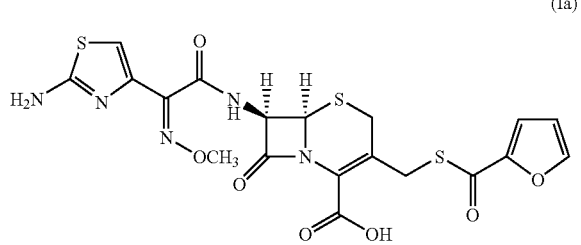

(Ia)

and its sodium salt of formula (Ib)

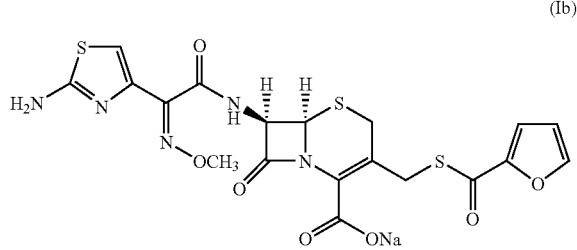

(Ib)

are valuable antibiotics for veterinary use, specially for treatment of infections in bovine animals.

The synthesis of ceftiofur (Ia) and cefiofur sodium (Ib) has been achieved the following ways:

1. U.S. Pat. No. 4,464,367, which covers ceftiofur and ceftiofur sodium, discloses two methods for preparation of ceftiofur, which comprises:

i) reaction of 7-amino-cephalosporanic acid (7-ACA) with (tritylamino-2-thiazolyl-4)-2-methoxyimino-2-acetic acid in presence of diccyclohexylcarbodiimide and hydroxy-1-benzotriazole, followed by reaction of the 7-acylated cephalosporanic acid thus obtained, with thiofuroic acid, followed by removal of the trityl protective group by treatment with trifluoroacetic acid to give ceftiofur (Ia) as summarized in Scheme-I This method is not only uneconomical but also poses serious safety hazards since it utilizes expensive and toxic dicyclohexylcarbodiimide for the coupling step and corrosive trifluoroacetic acid for removal of the amino protective group. Moreover, the by-product formed in the reaction, viz. dicyclohexyl urea is not easily removed requiring, more often than not tedious and elaborate purification methods.

ii) reaction of 7-[2-(2-amino-4-thiazolyl)-2-methoxyimino acetamido] cephalosporanic acid, generically known as cefotaxime of formula (IV) with thiofuroic acid to give ceftiofur (Ia) as summarized in Scheme-II.

The conversion of cefotaxime to ceftiofur, which involves nucleophilic displacement of the acetoxy substituent (—OCOCH$_3$) at 3α-position of the former compound with a thiofuroyl group (—S—CO—C$_4$H$_3$O) can be carried out in the presence of an acid or in the presence of a base Substitution of an acetoxy function (—OCOCH$_3$) by a thiofuroyl group (—S—CO—C$_4$H$_3$O) can be achieved through a S$_N$1 or S$_N$2 reaction but the success of these reactions strictly depends on various parameters. In the case of cephalosporin compounds, such a S$_N$1 or S$_N$2 reaction is highly dependent on the pH of the reaction i. e. whether it is carried out in the presence of an acid or a base, the medium of reaction, temperature of reaction etc.

However, apart from a cursory mention of the abovementioned reaction sequence summarized in Scheme-II, the U.S. Pat. No. 4,464,367 neither provides any detail whatsoever nor any enabling conditions for preparation of ceftiofur from cefotaxime, either through an example or description.

Whatever is mentioned is nothing but a conjecture with no evidence whatsoever to substantiate the conjecture, which would be evident from the discussion in the later part of this specification.

Scheme-I:
Synthesis of Ceftiofur as per Method-I disclosed in U.S. Pat. No. 4,464,367

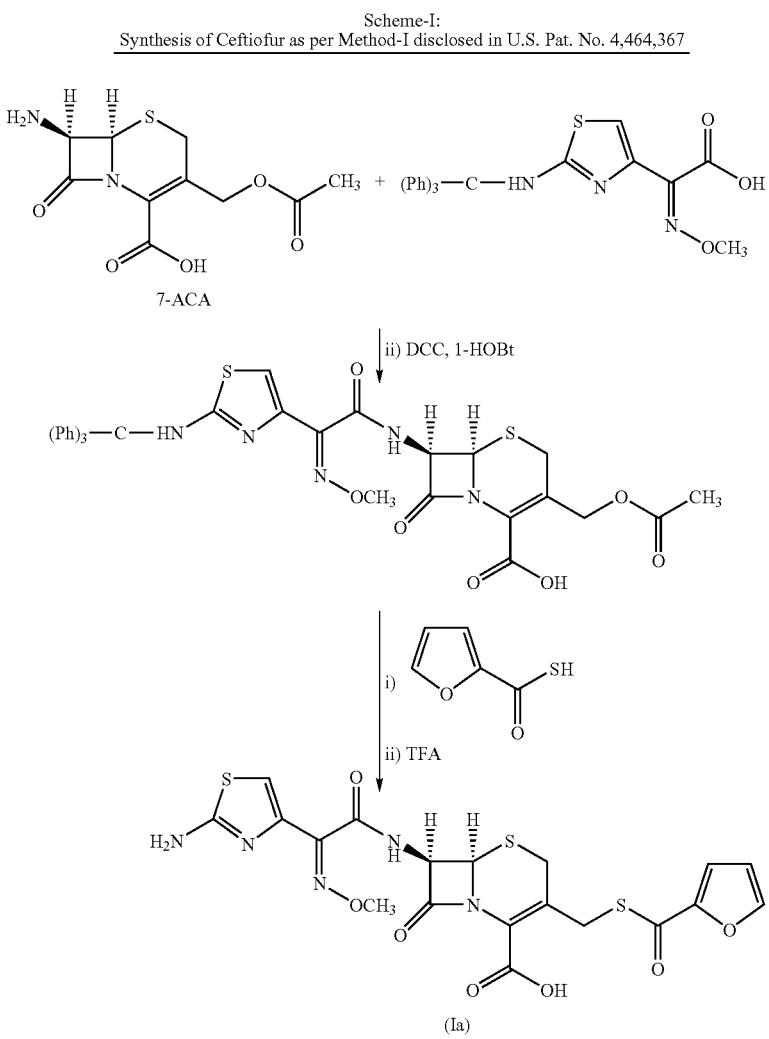

Scheme-II:
Synthesis of Ceftiofur as per Method-II disclosed in U.S. Pat. No. 4,464,367

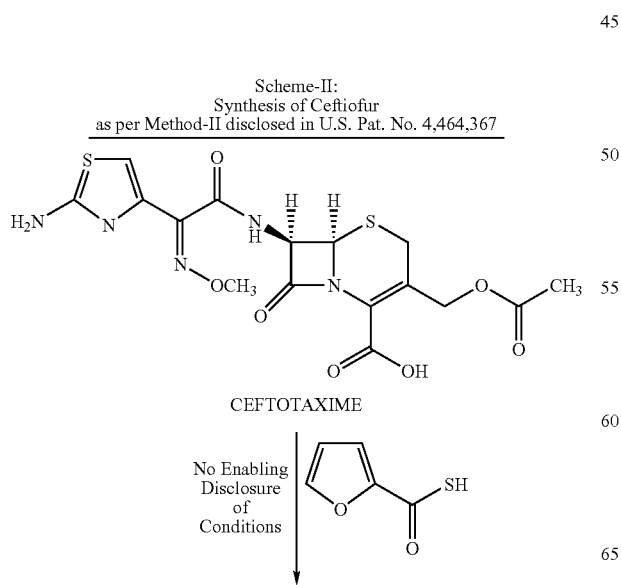

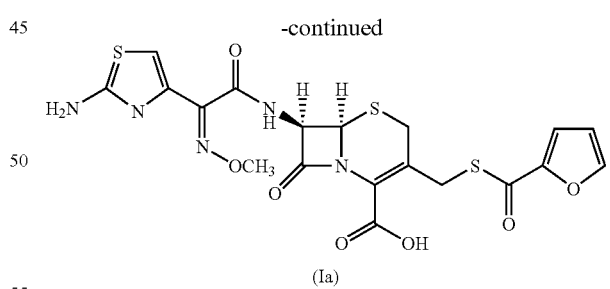

Further, the thiofuroyl substituent at 3α-position of the product i. e. ceftiofur is very vulnerable to acidic as well as basic conditions resulting in hydrolysis of furoyl group to give thiol (—SH) derivative at the 3α-position as well as formation of divalent sulfur derivatives. This makes it very difficult to effect a successful $S_N1$ or $S_N2$ substitution at the 3α-position of cefotaxime to obtain ceftiofur substantially free of the thiol compound and the divalent sulfur derivatives.

The problem is further compounded by the presence of the 2-[(2-amino thiazol-4-yl)-methoxyimino]acetamido addendum at the 7-position, which is also highly susceptible to cleavage under acidic and basic conditions to give the corresponding 7-deacylated derivative i. e. 7-free amino derivative.

The U.S. Pat. No. 4,464,367 further states that mineral salts of the corresponding acids are obtained by action on the free acid of formula (Ia) with a mineral base such as NaOH or KOH or NaHCO$_3$ in equimolar quantity; the salification reaction is effected in a solvent such as water or ethanol and the salt obtained is isolated by evaporation of the solution.

However, there is no enabling disclosure in the patent specification for methods for preparation of ceftiofur sodium.

2. U.S. Pat. No. 4,937,330 describes a method for preparation of ceftiofur sodium of high purity comprising the steps of:
   i) conversion of ceftiofur to a crystalline ceftiofur hydrohalide salt, specially the hydrochloride salt,
   ii) neutralization of the crystalline hydrohalide salt of ceftiofur, specially the hydrochloride salt thus obtained by treatment with a basic resin eg. polyvinyl pyridine in an aqueous organic solvent,
   iii) removal of the basic resin from the reaction mixture by filtration, and
   iv) treating the filtrate containing the neutralised compound i. e. ceftiofur with a base of a sodium metal carrier to give ceftiofur sodium.

However, this method is not only lengthy and less cost-effective since it involves the step of formation of a hydrochloride salt and its subsequent neutralization and utilization of expensive resins like polyvinyl pyridine.

3. U.S. Pat. No. 6,458,949 describes a process for preparation of ceftiofur sodium and its intermediates comprising reaction of silylated 7-amino-3-(2-furylcarbonylthiomethyl)-3-cephem-4-carboxylic acid (furaca) with 4-halo-2-methoxyimino-3-oxobutyryl halide to give an intermediate, which on cyclization with thiourea gives ceftiofur as summarized in Scheme-III.

However, this method involves a total of 6 steps, of which 4 steps are involved to prepare the 4-halo-2-methoxyimino-3-oxobutyryl halide intermediate, making it lengthy and tedious. Moreover, the yields reported are low rendering the process commercially not very attractive.

Scheme-III:
Synthesis of ceftiofur as per the method disclosed in U.S. Pat. No. 6,458,949

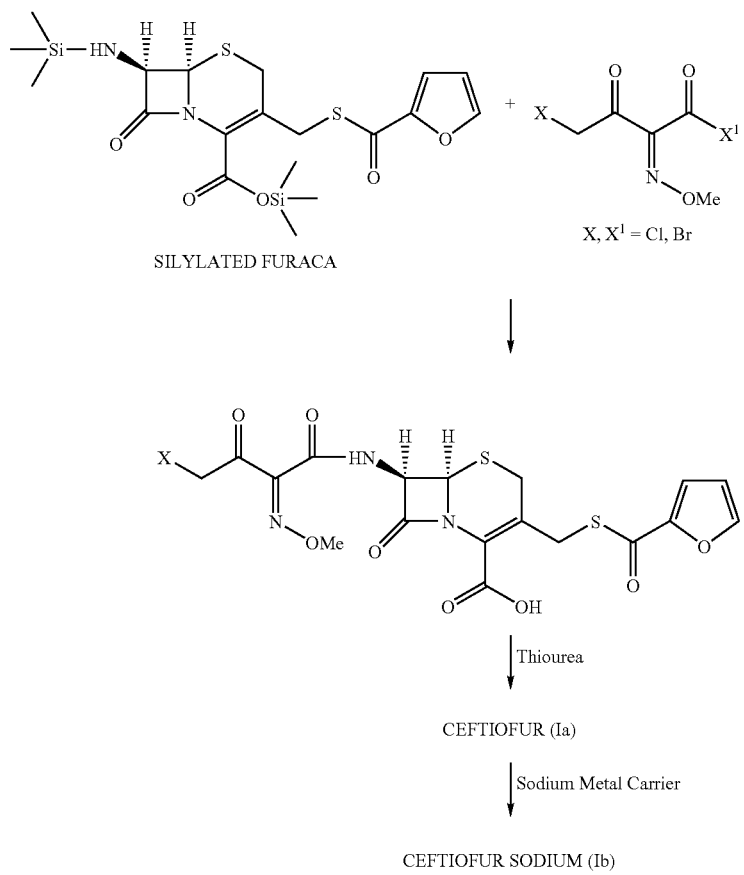

4. Displacement of a functional group at of 3α-position of a cephalosporin derivative to give a 3-thiomethyl derivative is known in the art. Notable among such methods are:

i) the one disclosed in U.S. Pat. No. 4,312,986 for a process for producing a 7-(substituted)-amino-3-substituted thiomethyl-Δ³-cephem-4-carboxylic acid derivative of the formula (II) comprising,

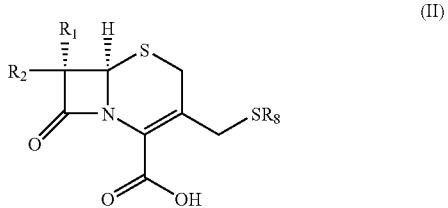

(II)

reaction of the compound of general formula (III),

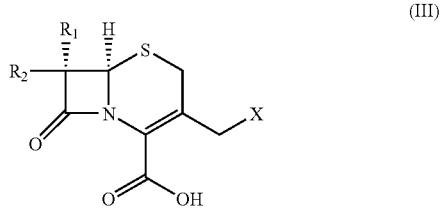

(III)

wherein $R_1$ is a hydrogen atom or a $C_{1-4}$ alkoxy group; $R_2$ inter alia is essentially an amino group and X is a leaving group with a thiol compound of formula $R_8$—SH, where $R_8$ is a thiol compound residue, in an organic solvent in the presence of a Bronsted acid, or a Lewis acid or complex compound of Lewis acid other than $BF_3$.

ii) the one disclosed in U.S. Pat. No. 6,476,220 for preparation of 7-amino-3-(2-furanylcarbonylthiomethyl)-3-cephem-4-carboxylic acid starting from 7-amino cephalosporanic acid and thiofuroic acid, by nucleophillic substitution of the acetoxy function at 3-position of the cephalosporin nucleus in (II) with a thiofuroyl function, as shown hereinbelow.

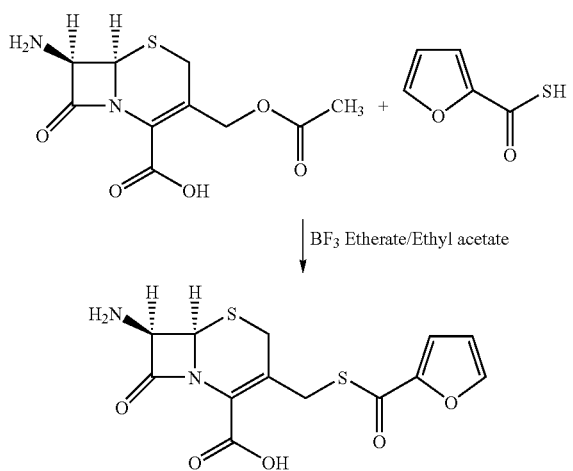

This displacement reaction is carried out in the presence of boron trifluoride in ethyl acetate. Since boron trifluoride is a gas, and hazardous in nature, it requires special handling precautions on an industrial scale.

However, the above patents essentially teach the functionalisation at 3-position of compounds of formula (II) and 7-ACA, which have a free amino group at 7-position of the cephalosporin nucleus. There is, however, no suggestion that 7-acylamino cephalosporins, specially those carrying a 2-aminothiazoylyl acetamido moiety at the 7-position could be reacted with a thiol compound, $R_8$—SH, in the presence of Bronsted acids or Lewis acids, to give the corresponding 7-(2-aminothiazolyl)-acetamido-3-substituted thiol derivative.

Further, Bronsted acids or Lewis acids are known to effect the cleavage of the amide bond at 7-position of cephalosporins. Incidentally, U.S. Pat. No. 5,132,419 relates to a process for preparation of 7-amino-3-[(Z)-1-propen-1-yl]-3-cephem-4-carboxylic acid of formula (V), by reaction of the corresponding 7-acyl amino derivative of formula (IV), wherein the cleavage of the amide bond at 7-position is effected by utilization of a Bronsted acid or Lewis acid. The chemistry is summarized hereibelow,

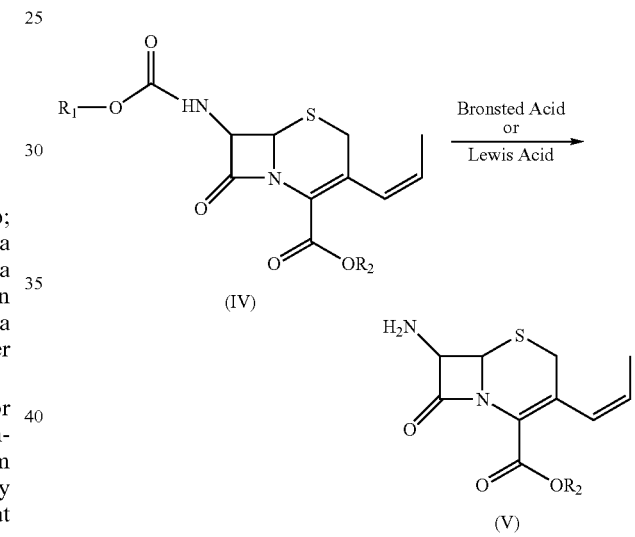

wherein $R_1$ and $R_2$ represents alkyl, aryl and aralkyl radicals, either identical or different.

Incidentally, the above fact was substantiated by the present inventors when in their attempts to convert cefotaxime to ceftiofur in the presence of a Lewis acid like Boron trifluoride etherate, the 7-deacylated derivative of cefotaxime i. e. 7-ACA was the major product, with very little conversion to ceftiofur observed.

From the foregoing, it is abundantly clear that:

a) while displacement of a functional group at of 3α-position of a cephalosporin derivative by reaction with a thiol compound in the presence of a Bronsted acid or a Lewis acid to give the corresponding 3-thiomethyl derivative is achieved, when the 7-amino function is unsubstituted i. e. is free;

b) the corresponding displacement of a functional group at of 3α-position of a cephalosporin derivative, wherein the 7-amino function is substituted i. e. carrying an acylamino function by reaction with a thiol compound in the presence of a Bronsted acid or a Lewis acid would be expected to lead to substantial cleavage of the 7-acylamino function or the amide bond to give the respective starting compounds with a free 7-amino group, with little or no displacement reaction taking place at the 3α-position.

Against this backdrop, reaction of compound of formula ((III), wherein the 7-amino function is substituted, specially with a 2-aminothiazolyl acetic acid moiety with the thiol compound, $R_8$—SH in the presence of a Bronsted acid or a Lewis acid would be expected to cleave the amide bond at 7-position leading to formation of the deacylated products, with little or no displacement reaction taking place at the 3α-position.

Indeed, the present inventors found it to be true when 7-[2-(2-amino-4-thiazolyl)-2-methoxyimino acetamido] cephalosporanic acid i.e. cefotaxime or its salts or its easily hydrolysable esters of formula (VI), (VI)

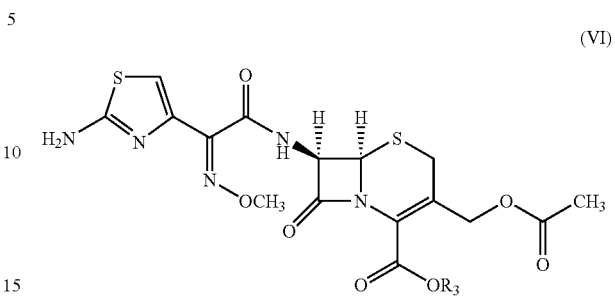

wherein $R_3$ is hydrogen, an alkali or alkaline earth metal, or an easily hydrolysable ester, is reacted with thiofuroic acid, in the presence of a Lewis acid such as aluminium chloride; boron trifluoride; zinc halides such as zinc chloride and zinc bromide; tin halides such as stannic chloride and stannic bromide; or the complex compounds of these Lewis acids with dialkyl ethers, amines, fatty acids, nitriles, carboxylic esters and phenols etc. very little displacement at the 3α-position took place and the reaction led to formation of predominant amounts of the 7-deacylated derivative i. e. 7-ACA, and unidentified impurities. Ceftiofur of formula (I) formed in the reaction was only between 5-15% and could not be isolated from the reaction mixture.

Similarly, when instead of a Lewis acid, the abovementioned reaction was carried out in the presence of a Bronsted acid like hydrochloric acid, p-toluenesulfonic acid, benzenesulfonic acid, trifluoromethane sulfonic acid, naphthalene sulfonic acid, super acids such as perchloric acid, magic acid ($FSO_3H$—$SbF_5$), $FSO_3H$—$AsF_5$, $CF_3SO_3$—H—$SbF_5$, $H_2SO_4$—$SO_3$, chloro sulfuric acid, fluoro sulfuric acid, etc. the same phenomena was observed i. e. very little displacement at the 3α-position took place and the reaction led to formation of predominant amounts of the 7-deacylated derivative i. e. 7-ACA, and unidentified impurities. Ceftiofur of formula (I) formed in the reaction was only between 5-20% and could not be isolated from the reaction mixture.

Further, carrying out the abovementioned reaction in the presence of a mixture of Bronsted acid and a Lewis acid was also found to result in predominant amounts of the 7-deacylated derivative i. e. 7-ACA, and impurities and here again whatever ceftiofur formed in the reaction could not be isolated from the reaction mixture.

The above conversion, hence, has no commercial application, except may be of some academic interest.

Against this backdrop, it was with surprising effect that the present inventors found that the reaction of 7-[2-(2-amino-4-thiazolyl)-2-methoxyimino acetamido] cephalosporanic acid i.e. cefotaxime or its salts or its easily hydrolysable esters of formula (VI), wherein $R_3$ is hydrogen, an alkali or alkaline earth metal, or an easily hydrolysable ester, (VI)

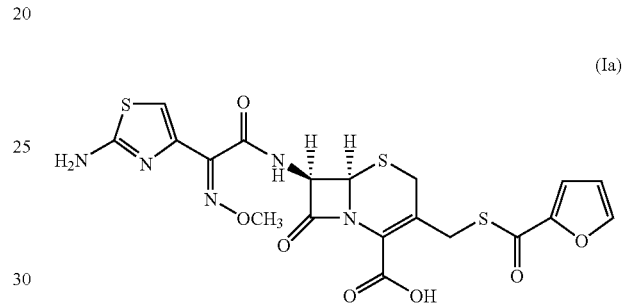

with thiofuroic acid can be carried out selectively to give a conversion to ceftiofur of formula (Ia), (Ia)

between 40% to 70% when the said reaction is carried out in the presence of either methanesulfonic acid or sulfuric acid.

However, again to their surprise the present inventors found that while the reaction of ceftotaxime with thiofuroic acid in the presence of sulfuric acid indicated a conversion of between 40 to 55% to ceftiofur, and formation of impurities in the range of between 8 to 40%, however, no product could be isolated from the reaction mixture, in spite of employing various isolation methods.

A dramatic change was found when methanesulfonic acid was used as the Bronsted acid instead of sulfuric acid. Not only a conversion of between 50 to 70% was achieved, but most importantly, ceftiofur could be indeed be isolated from the reaction mixture in substantially large amounts and surprisingly the isolated product was found to possess high stability, high purity of more than 97% and found to be substantially free of impurities.

More surprising was the finding that though methanesulfonic acid gives a commercially viable conversion of cefotaxime to ceftiofur conforming to pharmacopoeia specification, other organic sulfonic acids like benzenesulfonic acid, p-toluenesulfonic acid, trifluoromethanesulfonic acid etc. failed miserably to give a viable process.

The yield and quality of ceftiofur and formation of impurities in the abovementioned reaction was also found with surprising effect to be highly dependent on the amount of methanesulfonic acid employed, the amount of thiofuroic acid employed, the medium and temperature of reaction. The selection of the molar proportions of methanesulfonic acid, the medium of reaction and the temperature of reaction in providing ceftiofur (Ia) in large isolable yields and high purity, therefore forms the basis of the present invention.

It was found that ceftiofur of formula (Ia) and ceftiofur sodium of formula (Ib) could be obtained in isolable yields of between 20% to 25% possessing high storage stability and having purity more than 97% and substantially free of impurities through a selection of parameters in the reaction of 7-[2-(2-amino-4-thiazolyl)-2-methoxyimino acetamido] cephalosporanic acid i.e. cefotaxime or its salts or its easily hydrolysable esters of formula (VI) with thiofuroic acid, the selection being utilization of:

i) not a catalytic amount but a large excess of methanesulfonic acid in molar proportions of 12-18 moles per mole of compound of formula (VI),
ii) an excess of thiofuroic acid in molar proportions of 1.5 to 3.0 moles per mole of compound of formula (VI),
iii) specifically acetonitrile as the medium of reaction, and
iv) a reaction temperature in the range of between −5° C. to 30° C., preferably between 10° C. to 30° C., and more preferably between 15° C. to 25° C.

It was further found that the ceftiofur (Ia) thus obtained could be converted to tis sodium salt i. e. ceftiofur sodium of formula (Ib), again possessing high storage stability and having purity more than 97% and substantially free of impurities through a selective method comprising double decomposition of a salt of ceftiofur with an organic amine with a sodium metal carrier and isolation of ceftiofur sodium from the reaction mixture through a solvent precipitation method.

Preparation of ceftiofur sodium (Ib) of high storage stability and having purity more than 97% and substantially free of impurities from cefotaxime (VI), via the intermediacy of ceftiofur (Ia), forms the basis of another aspect of the present invention.

The ceftiofur (Ia) and its sodium salt (Ib), thus obtained by virtue of their high purity and stability are found to be highly suitable for formulation into suitable dosage forms.

SUMMARY OF THE INVENTION

In one aspect, the present invention provides an improved method for preparation of ceftiofur of formula (Ia),

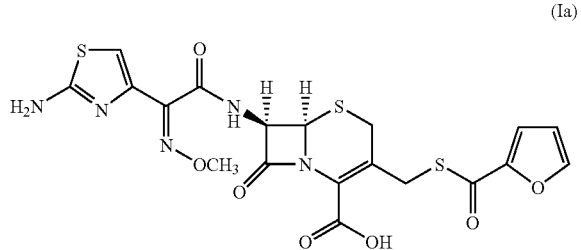

(Ia)

possessing high stability and having purity of more than 97% and substantially free of impurities, comprising reaction of cefotaxime or its salts or its esters of formula (VI)

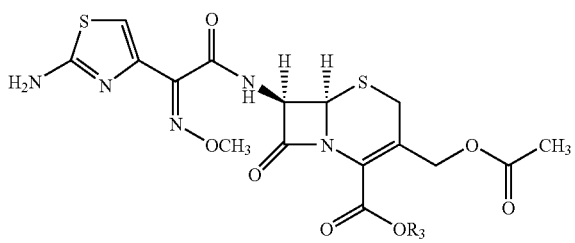

(VI)

wherein $R_3$ is hydrogen, an alkali or alkaline earth metal, or an easily hydrolysable ester, with thiofuroic acid, employed in a molar proportion of 1.5 to 3.0 moles per mole of compound (VI), in the presence of acetonitrile as solvent and in the presence of large excess of methanesulfonic acid, employed in molar proportions of 12 to 18 moles per mole of compound (VI), and at a temperature of between −5° C. to 30° C., preferably between 10° C. to 30° C., and more preferably between 15° C. to 25° C. to give ceftiofur of formula (Ia), after necessary neutralisation of the alkali or alkaline earth metal or removal of the ester group of the 4-carboxylic acid function, wherever applicable.

In another aspect, the present invention provides a process for preparation of ceftiofur sodium of formula (Ib), possessing high stability and having purity of more than 97% and substantially free of impurities, comprising

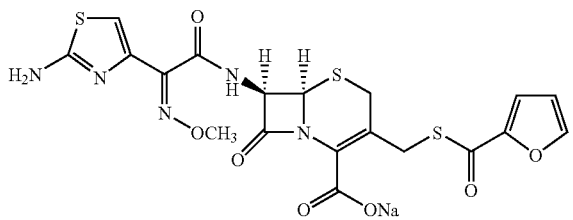

(Ib)

i) reaction of cefotaxime or its salts or its esters of formula (VI)

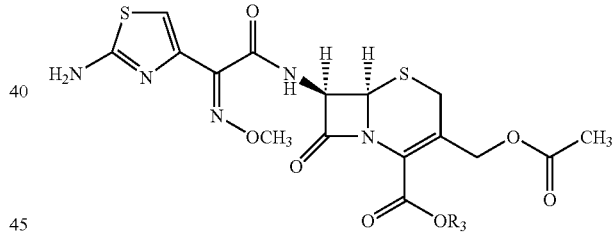

(VI)

wherein $R_3$ is hydrogen, an alkali or alkaline earth metal, or an easily hydrolysable ester, with thiofuroic acid, employed in a molar proportion of 1.5 to 3.0 moles per mole of compound (VI), in the presence of acetonitrile as solvent and in the presence of large excess of methanesulfonic acid, employed in molar proportions of 12 to 18 moles per mole of compound (VI), and at a temperature of between −5° C. to 30° C., preferably between 10° C. to 30° C., and more preferably between 15° C. to 25° C. to give ceftiofur of formula (Ia), after necessary neutralisation of the alkali or alkaline earth metal or removal of the ester group of the 4-carboxylic acid function, wherever applicable,
ii) converting the ceftiofur of formula (Ia) thus obtained to its salt with an organic amine by treating a solution of ceftiofur in a mixture of water and a water-miscible organic solvent with an organic amine, at a temperature ranging from −10° C. to 10° C.,
iii) reaction of the amine salt thus obtained with a sodium metal carrier in a mixture of water and water-miscible organic solvent in presence of sodium hydrogen sulfite to give ceftiofur sodium of formula (Ib)

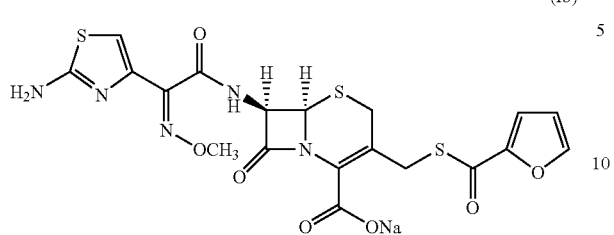

The selective method of preparation of ceftiofur (Ia) and ceftiofur sodium (Ib) as per the present invention is summarized in Scheme-IV for ready reference.

DETAILED DESCRIPTION OF THE INVENTION

In a typical embodiment of the present invention, cefotaxime, its alkali or alkaline earth metal salts or easily hydrolysable esters of formula (VI) is suspended in the inert organic solvent, to which methanesulfonic acid is added. To the resulting solution is added thiofuroic acid and the progress of the reaction is monitored by HPLC. After Scheme-IV:
Method of perparation of ceftiofur (Ia) and ceftiofur sodium (Ib) as per the present invention

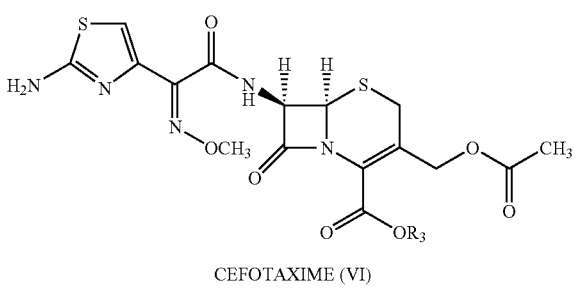

CEFOTAXIME (VI)

i) <image of furan-2-carbothioic acid> SH; 1.5 to 3.0 Moles ii) Methanesulfonic acid; 12–18 Moles
iii) inert organic solvent from acetonitrile, tetrahydrofuran, dichlormethane, 1,2-dichloroethane and ethyl acetate
iv) 10–30° C.

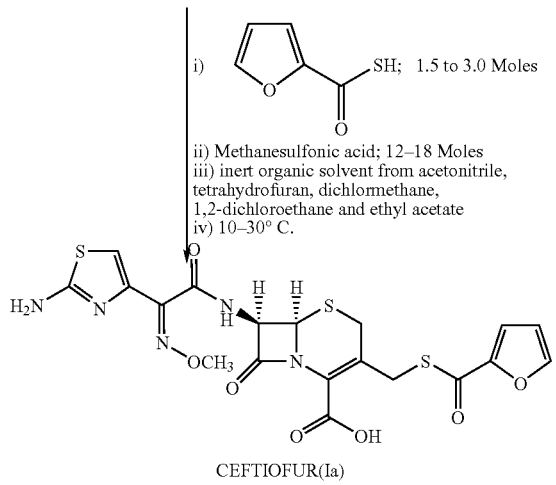

CEFTIOFUR(Ia)

i) water + water-miscible organic solvent
ii) Organic amine
iii) -10° C. to 10° C.
iv) Sodium metal carrier
v) sodium hydrogen sulfite

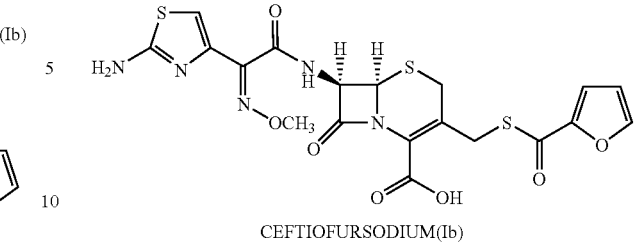

CEFTIOFURSODIUM(Ib)

completion of reaction the product i.e. ceftiofur of formula (Ia) is isolated by conventional methods, after neutralisation of the alkali or alkaline earth metal salts or removal of carboxylic acid protecting group, if any.

By easily hydrolysable esters of the compounds of formula (VI) there are to be understood compounds of the formula (VI) in which the carboxyl group is present in the form of an ester group which can be easily hydrolysed. Examples of such esters, which can be of the conventional type, are the lower alkanoyloxyalkyl esters, e.g., the acetoxy methyl, pivaloxymethyl, 1-acetoxyethyl, 1-pivaloxyethyl ester; the lower alkoxycarbonyloxyalkyl esters, e.g., the methoxycarbonyloxymethyl, 1-ethoxycarbonyloxyethyl and 1-isopropoxycarbonyloxyethyl ester, the alkoxymethyl esters, e.g., methoxy methyl ester, and the lower alkylaminomethyl esters, e.g., the acetamidomethyl esters. Other esters, e.g. the benzyl and cyanomethyl esters can also be used.

Alkali metals are selected from sodium, potassium, lithium and cesium, while the alkali earth metals are selected from magnesium and calcium.

The role of each parameter of the method of the present invention i. e.
ii) Selection of methanesulfonic acid as the Bronsted acid,
iii) Selection of the molar proportion of methanesulfonic acid to be employed,
iv) Selection of the medium of reaction, and
v) Selection of the temperature of reaction in giving ceftiofur (Ia) in yields of 20-25%, having high storage stability and having purity greater than 97% and which, moreover, is substantially free of impurities is discussed in detail hereinbelow.

Selection of Methanesulfonic Acid as the Bronsted Acid

As mentioned hereinearlier, when 7-[2-(2-amino-4-thiazolyl)-2-methoxyimino acetamido] cephalosporanic acid i.e. cefotaxime or its salts or its easily hydrolysable esters of formula (VI) was reacted with thiofuroic acid, in the presence of a Lewis acid such as aluminium chloride; boron trifluoride, zinc halides such as zinc chloride and zinc bromide; tin halides such as stannic chloride and stannic bromide or the complex compounds of these Lewis acids with dialkyl ethers, amines, fatty acids, nitriles, carboxylic esters and phenols etc. very little displacement at the 3α-position took place and the reaction led to formation of predominant amounts of the 7-deacylated derivative i. e. 7-ACA, and impurities. Ceftiofur of formula (I) formed in the reaction was only between 5-15% and could not be isolated from the reaction mixture.

Similarly, when instead of a Lewis acid, the abovementioned reaction was carried out in the presence of a Bronsted acid like hydrochloric acid, p-toluenesulfonic acid, benzenesulfonic acid, trifluoromethane sulfonic acid, naphthalene sulfonic acid, super acids such as perchloric acid, magic acid ($FSO_3H$—$SbF_5$), $FSO_3H$—$AsF_5$, $CF_3SO_3$—H—$SbF_5$, H₂SO₄—SO₃, chloro sulfuric acid, fluoro sulfuric acid, etc. the same phenomena was observed i. e. very little displacement at the 3α-position took place and the reaction led to formation of predominant amounts of the 7-deacylated derivative i. e. 7-ACA, and unidentified impurities. Ceftiofur of formula (I) formed in the reaction was only between 5-20% and could not be isolated from the reaction mixture.

In particular, when sulfuric acid was employed as the Bronsted acid in various molar proportions in the reaction of cefotaxime (VI) with thiofuroic acid in the presence of different solvents and at different temperatures, although the reaction inter alia was found to be slow, leading to conversion of ceftiofur of between 40% to 55% with concurrent formation of impurities in large amounts, no isolation of the product was possible even after utilizing various isolation methods.

On the other hand, when methanesulfonic acid is used the conversion to ceftiofur is found be more than 50%, specially in the range of 55-70%.

even after prolonged reaction time. Further, the product i. e. ceftiofur could not be isolated from the reaction mixture in both the cases.

When a large excess of methanesulfonic acid was employed in a molar proportion of 12-18 moles per mole of compound (VI) the reaction was found to proceed to completion with conversion to ceftiofur in the range of 55-70% and resulting in its isolation in a yield of 20-25%, with a purity of more than 97%.

This clearly shows that the role of methanesulfonic acid is not catalytic and the conversion requires a large excess of the acid to employed to obtain ceftiofur in isolable yields. Further, ceftiofur is obtained in isolable yields only when the molar proportion of methanesulfonic acid employed is more than 12 Moles, while anything below like utilization of 10 Moles, 8 Moles etc. no product could be isolated.

Selectivity of the molar proportions of the Bronsted acid in the method of the present invention is summarized in Table-II.

TABLE I

Results obtained on utilization of various Lewis acids and Bronsted acids in the reaction of compound of formula (VI) with thiofuroic acid

| No | The Acid used in Moles | Solvent | Temperature (° C.) | % Ceftiofur formed | % Impurities | Others | % Isolated Yield |
|---|---|---|---|---|---|---|---|
| 1 | Boron trifluoride Etherate (15 M) | Acetonitrile | 25 | 13.0 | 68.0 | — | Product could not be isolated |
| 2 | Sulfuric acid (15 M) | Acetonitrile | 15-20 | 46.0 | 48.0 | — | Product could not be isolated |
| 3 | Sulfuric acid (10 M) | Acetonitrile | 15-20 | 49.0 | 22.0 | 22% unreacted starting material | Product could not be isolated |
| 4 | Methanesulfonic acid (5 M) + Sulfuric acid (10 M) | Acetonitrile | 15-20 | 54.0 | 36.0 | — | Product could not be isolated |
| 5 | Methanesulfonic acid (15 M) | Acetonitrile | 15-20 | 62.0 | 15.0 | — | 25.0* |

*Purity: 98%

Further, by increasing the acidity by carrying out the abovementioned reaction in a mixture of methanesulfonic acid and trifluoroacetic acid or in the presence of methanesulfonic acid with a Lewis acid like zinc chloride was also found to result in predominant amounts of the 7-deacylated derivative i. e. 7-ACA, and impurities, again leading to no isolable product.

A comparison of the results obtained using various Lewis and Bronsted acids is summarized in Table-I.

Selection of the Molar Proportion of Methanesulfonic Acid

When methanesulfonic acid was employed in a molar proportion of 6 moles per mole of compound (VI) the reaction was found to be slow with about 49% of the starting material i. e. cefotaxime (VI) was found left unreacted. Likewise, when methanesulfonic acid was employed in a molar proportion of 8 moles per mole of compound (VI) about 15% of the starting material was found left unreacted,

TABLE-II

Effect of molar ratio of methanesulfonic acid in the conversion of cefotaxime (VI) to ceftiofur (Ia)

| Molar Proportion of methanesulfonic acid | % of unreacted starting material (VI) | % Isolated Yield (molar) of ceftiofur (Ia) |
|---|---|---|
| 6 M | 49.31 | Product could not be isolated |
| 8 M | 14.64 | Product could not be isolated |
| 15 M | 2.00 | 21.70 |

Selection of the Medium of Reaction

Although, any inert organic solvent which does not participate in the reaction can be employed, it was particularly found that only acetonitrile gives an optimum conversion to ceftiofur of more than 50%, in particular in the range of 55-70%.

When other inert solvents such as sulfolane, N,N-dimethylformamide, N,N-dimethylacetamide, tetrahydrofuran, dichloromethane, 1,2-dichloroethane, ethyl acetate etc. are employed, the reaction was either found not to proceed to completion or resulted in formation of higher level of impurities, with very little isolable amounts of ceftiofur.

The selectivity of acetonitrile over other inert solvents in providing optimum coversion to ceftiofur is summarized in Table-III.

Selection of the Temperature of Reaction

The reaction can typically be carried out at temperatures ranging from −30° C. to 30° C. The preferred temperature for achieving optimum conversion to ceftiofur (Ia) is between 10° C. to 30° C.

The effect of temperature in optimum conversion to ceftiofur is summarized in Table-IV.

Normally it would be expected that carrying out the reaction at lower temperatures would favour facile conversion with formation of lesser amount of impurities. However, the results obtained and summarized in Table-IV indicate that there is very little conversion at a low temperature of between 0° C. to 5° C. and formation of impurities is more than 70%. Similarly, when the temperature is high between 40° C. to 45° C., again there is very little conversion to ceftiofur with more than 70% impurities formed.

The most optimum temperature is between 10° C. to 30° C. and more preferably between 25° C. to 30° C.

TABLE III

The effect of solvent in the reaction of compound of formula (VI) with thiofuroic acid in the presence of methanesulfonic acid to give ceftiofur (Ia)

| | | Methane-Sulfonic acid Used in Moles | Temperature (° C.) | Results | | | |
|---|---|---|---|---|---|---|---|
| No | Solvent Used | | | % Ceftiofur formed | % Impurities | Others | % Isolated Yield |
| 1 | Sulfolane | 15.0 | 25-30 | 47.0 | 26.0 | 28% unreacted starting material | Product could not be isolated |
| 2 | Dichloro-Methane | 10.0 | 23-27 | 22.0 | 55.0 | — | Product could not be isolated |
| 3 | Ethyl acetate | 15.0 | 30 | 29.0 | 49.0 | 21% unreacted starting material | Product could not be isolated |
| 4 | Acetonitrile + Ethyl acetate (2:1) | 15.0 | 15 | 21.0 | 29.0 | 50% unreacted starting material | Product could not be isolated |
| 5 | Acetonitrile | 15.0 | 10-15 | 62.0 | 15.0 | — | 23.0* |
| 6 | Acetonitrile | 15.0 | 25-30 | 70.0 | 11.0 | — | 25.0** |

*Purity: 98%
**Purity: 99%

TABLE IV

Effect of temperature in the reaction of compound (VI) with thiofuroic acid to ceftiofur (Ia)

| | | Methane-Sulfonic acid Used in Moles | Temperature (° C.) | Results | | | |
|---|---|---|---|---|---|---|---|
| No | Solvent Used | | | % Ceftiofur formed | % Impurities | Others | % Isolated Yield |
| 1 | Acetonitrile | 15.0 | 10-15 | 62.0 | 15.0 | — | 23.0* |
| 2 | Acetonitrile | 15.0 | 25-30 | 70.0 | 11.0 | — | 25.0** |
| 3 | Acetonitrile | 15.0 | 0-5 | <10.0 | >70.0 | — | Product could not be isolated |

TABLE IV-continued

Effect of temperature in the reaction of compound
(VI) with thiofuroic acid to ceftiofur (Ia)

| No | Solvent Used | Methane-Sulfonic acid Used in Moles | Temperature (° C.) | Results % Ceftiofur formed | % Impurities | Others | % Isolated Yield |
|---|---|---|---|---|---|---|---|
| 4 | Acetonitrile | 15.0 | 40-45 | <10.0 | >70.0 | — | Product could not be isolated |

*Purity: 98%
**Purity: 99%

Thiofuroic acid can be employed in equimolar to excess of equimolar proportions of compound (VI). However, it is preferable to employ a slight excess of thiofuroic acid, preferably in a molar proportion of 1.5 to 3 moles per mole of the compound (VI);

In a typical method, to a solution of cefotaxime in acetonitrile cooled to 0-5° C. is added methanesulfonic acid, followed by thiofuroic acid and the temperature raised to 10-30° C. and the mixture agitated till completion of reaction, wherein the solid precipitates out.

Ceftiofur acid (Ia) thus produced can be isolated by conventional methods as described in U.S. Pat. No. 4,464,367 or U.S. Pat. No. 6,458,949.

However, it is preferably isolated by filtration of the precipitated solid and washing the solid, thus obtained with a water-immiscible organic solvent selected from $C_{1-4}$ esters of acetic acid, such as methyl acetate, ethyl acetate, propyl acetate, isopropyl acetate, butyl acetate, iso-butyl acetate, or tert-butyl acetate and adjusting the pH of the mixture to 3.0 to 3.5 by addition of aqueous HCl. The precipitate thus obtained is again washed with a mixture of water-miscible and water-immiscible organic solvent, followed by pH adjustment to about 7.0 by aqueous sodium carbonate solution. The aqueous and organic layers are separated and the solid is precipitated by addition of a non-polar solvent and collected by filtration and dried.

The water-miscible organic solvents that can be used are selected from acetone, tetrahydrofuran, acetonitrile, methanol and ethanol.

The non-polar solvents that can be used are selected from n-hexane, heptane, cyclohexane and toluene.

The ceftiofur (Ia), obtained by the present method has the following characteristics

| Purity | 97-99% |
|---|---|
| Total Impurities | 3.0-3.5% |
| Storage Stability | Stable for 90 days at 40° ± 2° C. with a drop in assay from 97% to 92% |

Preparation of Ceftiofur Sodium

Another aspect of the invention relates to a method for conversion of ceftiofur (Ia) thus obtained to the sodium salt i. e ceftiofur sodium of formula (Ib) in high yield, having high storage stability, having a purity of more than 97% and substantially free of impurities, through a selective, process described hereinbelow.

The ceftiofur acid (Ia), thus obtained is suspended in a mixture of water-miscible organic solvent and water, at a temperature, ranging between −10° C. to 10° C. and treated with an organic amine to obtain a solution of the salt of ceftiofur with the organic amine.

The amine salt thus obtained can be isolated, but preferably without isolation is reacted with a sodium metal carrier to give ceftiofur sodium of formula (Ib), which can be isolated by precipitation by addition of more amounts of the water-miscible organic solvent used. The method for preparation of ceftiofur sodium is shown hereinbelow.

Organic amines that can be used in the invention are selected from triethyl amine, diethyl amine, cyclohexyl amine, tertiary butyl amine, benzyl amine and the like. The organic amines are employed in molar proportions of 1.0 to 3.0 moles per mole of ceftiofur (Ia). Preferably they are employed in molar proportions of 1.2 to 1.5 moles per mole of ceftiofur (Ia).

The water-miscible organic solvents that can be used are selected from acetone, tetrahydrofuran, acetonitrile, methanol and ethanol.

Sodium metal carriers that can be employed can be either organic or inorganic These are selected from sodium hydroxide, sodium carbonate, sodium bi carbonate, sodium ethoxide, sodium-2-ethyl hexanoate, sodium acetate, sodium propionate or sodium salt of 2-ethylcaproic acid The product is isolated by precipitation through addition of excess of the water-miscible organic solvent into the reaction mixture.

In a typical method, to a suspension of ceftiofur (Ia) in a mixture of the water-miscible organic solvent and water cooled to −10° C. to 10° C. is added the organic base and the reaction mixture agitated for 30-45 minutes. The mixture treated with activated carbon and sodium dithionate and filtered.

To the filtrate is added a solution of the sodium metal carrier in the water-miscible organic solvent and the precipitated solid was collected by filtration to give ceftiofur sodium (Ib).

The ceftiofur sodium (Ib), obtained by the present method has the following characteristics

| Purity | 97-99% |
|---|---|
| Total Impurities | 2.0-2.5% |
| Storage Stability | Stable for 90 days at 40° ± 2° C. with a drop in assay from 94 to 87% |

Both the ceftiofur acid (Ia) and ceftiofur sodium (Ib) obtained by the process of the present invention by virtue of having high storage stability and purity of more than 97% are highly amenable for formulation into stable dosage forms.

The invention is further illustrated by the following non-limiting examples.

EXAMPLE-1

Preparation of 7-[2-(2-amino-4-thiazolyl) glyoxylamido] 3-(mercaptomethyl)-8-oxo-5-thia-1-azabicyclo-[4.2.0]oct-2-ene-2-carboxylic acid (ceftiofur, Ia) from 7-[2-(2-amino-4-thiazolyl)-2-methoxyimino acetamido] cephalosporanic acid (cefotaxime, VI) using methanesulfonic acid 20.0 g (0.044 moles) of 7-[2-(2-amino-4-thiazolyl)-2-methoxyimino acetamido] cephalosporanic acid (cefotaxime; VI, wherein $R_3$ is H) and acetonitrile (200 ml) was charged to a round bottom flask. The reaction mixture was cooled to 0-5° C. Methanesulfonic acid 62.0 g (0.643 moles) followed by thiofuroic acid (50.0 ml 0.066 moles) was added to the mixture and temperature raised to 10-15° C. Progress of the reaction was monitored by HPLC. After completion of reaction the reaction mixture was cooled to 0° C. and the precipitated solid was filtered and washed with 2×100 ml of ethyl acetate. The solid ceftiofur (Ia), thus obtained was taken in 200 ml of demineralized water, cooled to 10° C. and the pH was adjusted to 3.0 by addition of 10% HCl and the precipitated solid was filtered off.

The wet solid thus obtained was taken in 200 ml of demineralised water and cooled to 10° C. 100 ml of ethyl acetate and 40 ml of acetonitrile was added. The pH was adjusted to 7.0 by addition of aqueous sodium carbonate solution (17%). The pH of the solution was readjusted to 3.0 by dilute HCl (15%). The organic and aqueous layer were separated and the organic layer was added 100 ml of cyclohexane at 27° C. The solid was filtered and washed with cyclohexane (100 ml) to give 5.0 g (25%) of 7-[2-(2-amino-4-thiazolyl) glyoxylamido] 3-(mercaptomethyl)-8-oxo-5-thia-1-azabicyclo-[4.2.0]oct-2-ene-2-carboxylic acid (Ceftiofur Ia) having purity 97.3%.

EXAMPLE-2

Preparation of 7-[2-(2-amino-4-thiazolyl) glyoxylamido] 3-(mercaptomethyl)-8-oxo-5-thia-1-azabicyclo-[4.2.0]oct-2-ene-2-carboxylic acid (ceftiofur, Ia) from cefotaxime sodium (VI) using methanesulfonic acid 20 g (0.04192 moles) of cefotaxime sodium (VI, wherein $R_3$ is Na) and acetonitrile (200 ml) were charged in a round bottom flask at room temperature. Methanesulfonic acid (62 g, 0.642 moles) was added slowly to the reaction mixture. Thiofuroic acid (50 ml; 0.066 moles) was added to the reaction mixture in a single lot. The reaction mixture was stirred for three hours. Progress of reaction was monitored by HPLC. The reaction mixture was cooled to 0° C. and the solid filtered and washed with 2×100 ml ethyl acetate. The wet ceftiofur (Ia) was taken in taken in 200 ml of demineralised water, cooled to 10° C. and pH of the solution was adjusted to 3.0 by 10% HCl. The solution was filtered and washed with demineralised water.

The wet solid, without drying was taken in 100 ml of ethyl acetate and 40 ml of acetonitrile and pH of the solution is adjusted to 7.0 by addition of a 17% aqueous solution of sodium carbonate. The pH was readjusted to 3.0 by dilute HCl (15%). The organic and aqueous layers were separated and to the organic layer was added 400 ml of cyclohexane at 27° C. The solid was filtered and washed with 100 ml of cyclohexane to yield 5.0 g (25%) of 7-[2-(2-amino-4-thiazolyl) glyoxylamido] 3-(mercaptomethyl)-8-oxo-5-thia-1-azabicyclo-[4.2.0]oct-2-ene-2-carboxylic acid (ceftiofur) having purity of 97.11%.

EXAMPLE-3

Preparation of 7-[2-(2-amino-4-thiazolyl) glyoxylamido] 3-(mercaptomethyl)-8-oxo-5-thia-1-azabicyclo-[4.2.0]oct-2-ene-2-carboxylic acid (ceftiofur, Ia)) from 7-[2-(2-amino-4-thiazolyl)-2-methoxyimino acetamido] cephalosporanic acid (cefotaxime, VI) using methanesulfonic acid 100.0 g (0.22 moles) of 7-[2-(2-amino-4-thiazolyl)-2-methoxyimino acetamido] cephalosporanic acid (cefotaxime; VI, wherein $R_3$ is H) and acetonitrile (1000 ml) was charged to a round bottom flask. The reaction mixture was cooled to 0-10° C. Methane sulfonic acid 318.1 g (96.4 moles) followed by dry thiofuroic acid in ethyl acetate (245.0 ml) was added. Temperature of the reaction mixture was maintained between −4 to −1° C. The reaction mixture was stirred for 6 hours at 5-10° C. The temperature was raised to 20 to 25° C. in 10-15 minutes time and stirring was continued for 60 minutes. Progress of reaction was monitored by HPLC. After completion of reaction the reaction mixture was filtered and washed with 2×100 ml of ethyl acetate. The solid was semi-dried under suction. The wet solid was charged to 1000 mL of demineralized water. The pH was adjusted to 3.0 by 10% w/v aqueous sodium carbonate solution (30 mL) in 30 minutes at 10-15° C. The reaction was stirred for 30 minutes at 15-20° C. The solid was filtered and washed with demineralized water (100 mL).

The wet solid (150 g) was suspended in demineralized water (1000 mL) at 25-30° C. The mass was cooled to 10° C. and 10% w/v aqueous sodium carbonate solution was (38 mL) was added slowly (in 60 minutes time) at pH 7-7.5 to dissolution at 8 to 10° C. 500 mL of ethyl acetate at 8 to 10° C. was added followed by addition of 200 mL of acetonitrile at 8 to 10° C. The pH of the solution was adjusted to 3.0 by orthophosphoric acid (~22 mL) at 8 to 10° C. The temperature was raised to 10 to 15° C. and the layers were separated. The aqueous layer was extracted with mixture of ethyl acetate (500 mL) and acetonitrile (200 mL) at 10 to 15° C. The combined organic layers were washed with aqueous methanol containing 500 mL of demineralized water and 100 mL of methanol at 10 to 15° C. The reaction mixture was stirred for 30 minutes at 10 to 15° C. and the layers were separated.

1.0 g of activated carbon was added to organic layer and stirred for 30 minutes at 10 to 15° C. The reaction mixture was filtered and concentrated to ~300 mL at 20 to 25° C. vacuum, to which was added 200 mL of ethyl acetate followed by 500 mL of cyclohexane. The reaction mixture was stirred for 60 minutes at 25±2° C. The solid was filtered and washed with 200 mL of cyclohexane. The solid was dried under vacuum till moisture content is less than 4% to give 25.0 g (25% w/w) of 7-[2-(2-amino-4-thiazolyl) glyoxylamido] 3-(mercaptomethyl)-8-oxo-5-thia-1-azabicyclo-[4.2.0]oct-2-ene-2-carboxylic acid (Ceftiofur, Ia) having purity of 98%.

EXAMPLE-4

Preparation of ceftiofur sodium (Ib) from 7-[2-(2-amino-4-thiazolyl) glyoxylamido] 3-(mercaptomethyl)-8-oxo-5-thia-1-azabicyclo-[4.2.0]oct-2-ene-2-carboxylic acid (ceftiofur) (Ia)

140 ml of tetrahydrofuran (THF) and 4.0 ml of demineralised water (DMW) and 4.0 g (0.00764 moles) of 7-[2-(2- amino-4-thiazolyl) glyoxylamido] 3-(mercaptomethyl)-8-oxo-5-thia-1-azabicyclo-[4.2.0]oct-2-ene-2-carboxylic acid (ceftiofur, Ia) were taken in a flask and stirred. The reaction mixture was cooled and 0.81 g (0.0080 moles) of triethyl amine (TEA) was added. Activated carbon (0.60 g) and sodium dithionite (0.04 g) were added and the reaction mixture filtered through celite bed and washed with a mixture of THF and DMW. The filtrate was passed through 0.2μ filter paper and washed with THF (100 ml).

A solution of sodium-2-ethyl hexanoate (1.80 g, 0.01084 moles) was prepared in THF and passed through 0.2μ filter paper. This filtrate was added gradually to the solution of the triethylamine salt of ceftiofur, obtained above and the precipitated solid was filtered under nitrogen atmosphere. The wet cake was washed with THF, followed by washing with ethyl acetate (2×44 ml) and acetone (2×29 ml) and dried under nitrogen atmosphere for 30-45 minutes with occasional raking. The semi dry cake was dried in vacuum oven at 700 mmHg/40° C. till moisture content was 2.0% to give 3.48 g (87%) of Ceftiofur sodium (Ib) having purity of 98.0%

EXAMPLE-5

Preparation of ceftiofur sodium (Ib) from 7-[2-(2-amino-4-thiazolyl) glyoxylamido] 3-(mercaptomethyl)-8-oxo-5-thia-1-azabicyclo-[4.2.0]oct-2-ene-2-carboxylic acid (Ceftiofur, Ia)

1000 ml of THF and 70.0 ml of demineralised water (DMW) and 100.0 g (0.191 moles) of 7-[2-(2-amino-4-thiazolyl) glyoxylamido] 3-(mercaptomethyl)-8-oxo-5-thia-1-azabicyclo-[4.2.0] oct-2-ene-2-carboxylic acid (ceftiofur, Ia) were taken in a flask and stirred for 5 minutes. The mixture was cooled to −5° C. and 20.47 g (0.202 moles) of triethyl amine (TEA) was added at −5 to −3° C. in 60 minutes. Activated carbon (15 g) and sodium dithionite (1.0 g) were added and the reaction mixture was stirred at −5 to 0° C. for 60 minutes. The mixture was filtered through celite bed and washed with a mixture of THF and DMW (5:0.3 v/v; 530 mL). The filtrate was passed through 0.2μ filter paper and washed with THF (100 ml).

A solution of sodium-2-ethyl hexanoate (50.78 g, 0.305 moles) was prepared in THF and passed through 0.2μ filter paper. This filtrate was added gradually to the solution of triethylamine salt of ceftiofur, obtained above and the mixture was stirred at at 8-10° C. for 60 minutes and the precipitated solid filtered under nitrogen atmosphere. The wet cake was slurry washed with THF (500 mL), followed by ethyl acetate (2×500 ml) and acetone (3×500 ml). The wet cake was dried under nitrogen atmosphere for 30-45 minutes with occasional raking. The semi dry cake was dried in vacuum oven at 700 mmHg/40° C. to give 88 g (0.88% w/w) of ceftiofur sodium (Ib), having a purity of 98%.

We claim:

1. A process for preparation of ceftiofur sodium of formula (Ib) having purity of more than 97% comprising the steps of:

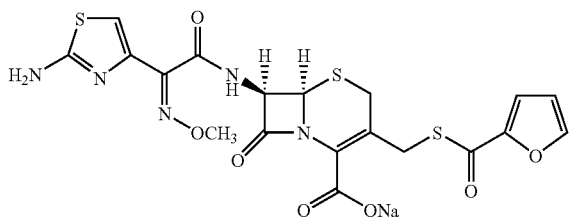

(Ib)

i) reacting cefotaxime or its salts or its esters of formula (VI)

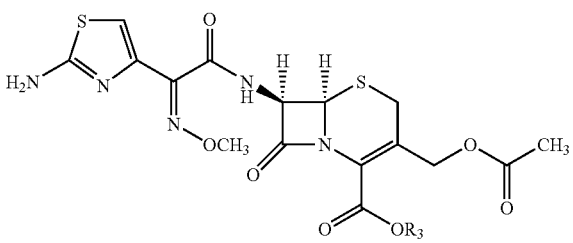

(VI)

wherein R₃ is hydrogen, an alkali or alkaline earth metal, or an ester hydrolysable under the conditions of step i), with thiofuroic acid, employed in a molar proportion of 1.5 to 3.0 moles per mole of compound (VI), in the presence of acetonitrile as solvent and in the presence of methanesulfonic acid, employed in molar proportions of 12 to 18 moles per mole of compound (VI), and at a temperature of between −5° C. to 30° C. to give after necessary neutralisation of the alkali or alkaline earth metal or removal of the ester group of the 4-carboxylic acid function, wherever applicable, ceftiofur of formula (Ia), having purity of more than 97%;

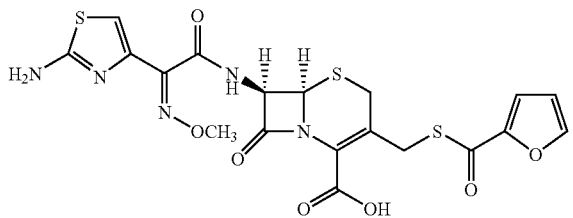

(Ia)

ii) converting the ceftiofur of formula (Ia) to its salt with an organic amine by treating a solution of ceftiofur in a mixture of water and a water-miscible organic solvent with an organic amine, at a temperature ranging from −10° C. to 10° C.;

iii) reacting the amine salt thus obtained with a sodium metal carrier in a mixture of water and water-miscible organic solvent and in presence of sodium hydrogen sulfite to give ceftiofur sodium of formula (Ib).

2. The process according to claim 1, wherein the temperature of step i) is between 10° ° C. to 30° C.

3. The process according to claim 1, wherein the water-miscible organic solvent is selected from the group consisting of acetone, tetrahydrofuran, acetonitrile, methanol and ethanol.

4. The process according to claim 1, wherein the organic amine is selected from the group consisting of triethyl amine, diethylamine, cyclohexylamine, tertiary butyl amine and benzyl amine.

5. The process according to claim 4, wherein the organic amine is employed in molar proportions of 1.0 to 3.0 moles per mole of ceftiofur (Ia).

6. The process according to claim 1, wherein the sodium metal carrier is selected from the group consisting of sodium hydroxide, sodium carbonate, sodium bicarbonate, sodium ethoxide, sodium acetate, sodium propionate, sodium 2-ethyl hexanoate, and sodium 2-ethylcaproate.

7. The process according to claim 1, wherein the hydrolysable ester is selected from the group consisting of lower alkanoylalkyl esters; lower alkoxycarbonyloxyalkyl esters; alkoxymethyl esters, lower alkylaminomethyl esters, benzyl ester, and cyanomethyl ester.

8. The process according to claim 1, wherein the temperature of step i) is between 15° C. to 30° C.

9. The process according to claim 4, wherein the organic amine is employed in molar proportions of 1.2 to 1.5 moles per mole of ceftiofur (Ia).

* * * * *

UNITED STATES PATENT AND TRADEMARK OFFICE
CERTIFICATE OF CORRECTION

PATENT NO. : 7,335,767 B2 Page 1 of 1
APPLICATION NO. : 10/694619
DATED : February 26, 2008
INVENTOR(S) : Om Dutt Tyagi et al.

It is certified that error appears in the above-identified patent and that said Letters Patent is hereby corrected as shown below:

On title page, item 30, "938/02" should read -- 938/MUM/02 --.

Signed and Sealed this

Seventeenth Day of June, 2008

JON W. DUDAS
*Director of the United States Patent and Trademark Office*